United States Patent
Stielau

Patent Number: 6,102,847
Date of Patent: Aug. 15, 2000

[54] BIO-FEEDBACK PROCESS AND DEVICE FOR AFFECTING THE HUMAN PSYCHE

[76] Inventor: Günter Stielau, Doristrasse 1, 153D6 Alt Rosenthal, Germany

[21] Appl. No.: 09/091,803
[22] PCT Filed: Dec. 19, 1996
[86] PCT No.: PCT/DE96/02470
  § 371 Date: Jun. 22, 1998
  § 102(e) Date: Jun. 22, 1998
[87] PCT Pub. No.: WO97/23160
  PCT Pub. Date: Jul. 3, 1997

[30] Foreign Application Priority Data

Dec. 22, 1995 [DE] Germany ............... 195 49 297

[51] Int. Cl.⁷ ............................................. A61M 21/00
[52] U.S. Cl. ............................................. 600/27
[58] Field of Search .................................. 600/26–28

[56] References Cited

U.S. PATENT DOCUMENTS 3,967,616  7/1976  Ross.
4,456,347  6/1984  Stahly.

FOREIGN PATENT DOCUMENTS

| 0076125 | 4/1983 | European Pat. Off. |
| 3546052 | 6/1987 | Germany. |
| 4234926 | 5/1994 | Germany. |
| 9405523 | 7/1994 | Germany. |
| 4307790 | 9/1994 | Germany. |
| 9117704 | 11/1991 | WIPO. |
| 9302616 | 2/1993 | WIPO. |

*Primary Examiner*—John P. Lacyk
*Attorney, Agent, or Firm*—Christie, Parker & Hale, LLP

[57] ABSTRACT

A bio-feedback process for affecting the human psyche and a device for implementing it comprises measuring eye movements, physiological parameters of eye muscles and/or nose root muscles of a person sensors. The measurements are transmitted to an evaluation system, which, by means of the measurements made in the immediate vicinity of the eyes and information stored in the evaluation system, assesses the psychological condition of the person. Depending on the data measured, the person is then stimulated by a stimulation system with relaxing or tensing stimuli. It is thus possible to relax or stimulate a person's psyche in a targeted manner, whereby the person's psychological condition can be easily and accurately measured in the immediate vicinity of the eye.

21 Claims, 2 Drawing Sheets

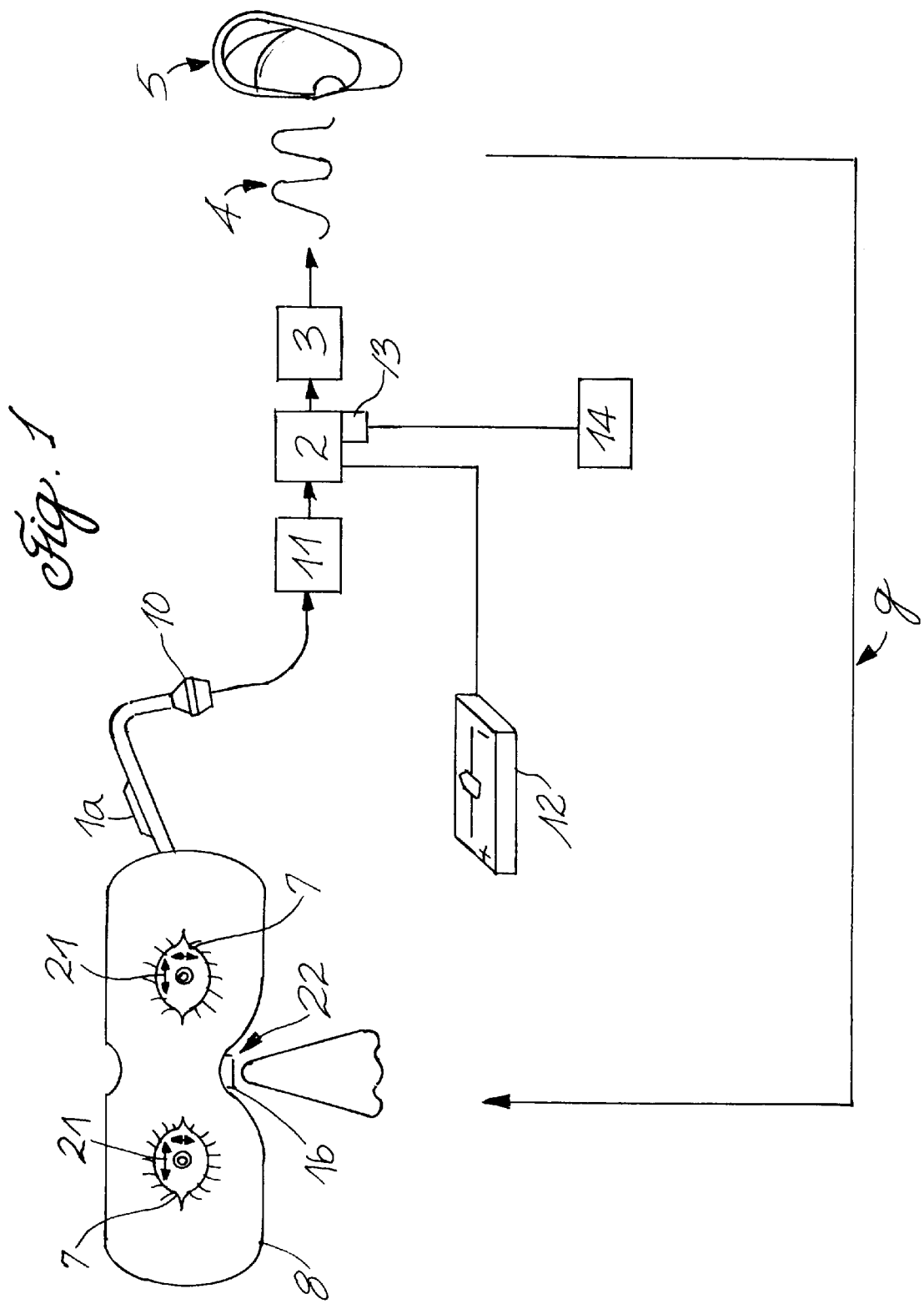

BIO-FEEDBACK PROCESS AND DEVICE FOR AFFECTING THE HUMAN PSYCHE

DESCRIPTION

The invention relates to a biofeedback process and a device for implementing the biofeedback process.

Nowadays people are suffering more and more from psychological strains which are caused for example through increased professional and private demands. These psychological strains are also called 'stress'. It is a generally known fact that the capability of a person is impaired when under the influence of stress. However other psychologically conditioned disorders such as for example difficulty in learning to read and write are also occurring more frequently nowadays.

For this reason processes and devices are required which act on the human psyche and thus help to break down stress or to generally improve performance and capability.

From DE 94 05 523.8 U1 a biofeedback device is known for learning or re-learning muscle activities or for relaxing muscles. Measured values are thereby derived from the electrical activity of the forehead muscles of a person. This has the disadvantage that the relaxation state of a person can only be measured from the forehead muscles. More particularly the eye area which is particularly useful in judging the tension or stressed state of a person is not detected since muscles in the eye area operate independently of the forehead muscles.

From DE 35 46 052 A1 a process and device are known through which the capacity of a person can be increased through the effect of music. The musical rhythm is thereby changed until it is in a harmonic (i.e. whole-numbered) ratio with the heart rhythm of the person. The drawback here is that both the rhythm of the heart and the rhythm of the music have to be monitored which requires a considerable apparatus expense. Also the adjustment of a harmonic ratio between the heart and music rhythms can be difficult since both rhythms are constantly changing.

DE 43 07 790 A1 discloses an apparatus for carrying out various psychotherapeutic methods. A person thereby lies in a relaxed state on a type of couch whereby the person is covered by a cover through which individual parts of the body can be targeted and brought to the right temperature. The couch contains sensors for measuring the skin temperature and the pulse rate and the measured results are sent to a computer-assisted control device. An evaluation of the relaxation state of the person is obtained from the measurements.

From DE 42 34 926 A1 a relaxation device is known where light and sound signals act on a person. In particular this apparatus is characterized in that the phases of the optical and acoustic signals are coupled with each other. Such a coupling is produced for example through matching the light signals to the basic rhythm of the music which is transferred to the patient. With this apparatus there is the drawback that no feedback exists so that the action on the person is carried out regardless of the momentary psychological tension state of the person.

From U.S. Pat. No. 4,456,347 a biofeedback device is known with sensors which receive reflections of a ray of light-emitting diode directed to the eye. Each movement of the eyes thereby causes a change in the output signal of the sensors. If the eye movement exceeds a predefined threshold value then an acoustic or tactile signal is produced. The signal is thereby produced until the eye movement is minimized so far that it lies below the predefined threshold value. If the eye movement lies below the predefined threshold value then no acoustic or tactile signal is produced.

Based on this prior art the object of the present invention is to provide a biofeedback process for producing acoustic and/or optical signals for relaxation purposes and a device for implementing the process which allows a continuous affect on the psyche of a person in targeted manner wherein the psychological state of the person can be measured easily and reliably in the immediate vicinity of the eyes. Furthermore no great apparatus expense is to be necessary for carrying out the measurements and influencing measures and these influencing measures can be readily adapted to the relevant psychological state of each person.

Thus according to the invention the eye movements of a person are measured electrically by detecting the action potentials in the eye or nose root area by means of suitable sensors since it has been shown that from this evidence can be readily gained on the psychological state of a person, particularly on the stressed state. The measured data detected is transferred to an evaluation system which produces on the basis of the measured values and information allotted to the measured values and stored in the evaluation system, control signals for a stimulation system in which acoustic and/or optical signals are continuously produced which are perceived by the person whereby effects are produced on the psychological state of the person (biofeedback).

The invention is based on the new and surprising knowledge that the eye moment as a parameter of the psychological state and as a starting value of a biofeedback process represents a suitable value which can be detected without great apparatus expense. By affecting the eye movement within the scope of the biofeedback process it is possible to influence in targeted manner the psychological state of a person.

The detection and processing of the measured values takes place in the evaluation system. The evaluation system receives and stores not only the measured values but it also has means (e.g. programs or specially programmed processors) which evaluate the measured values with regard to the psychological state. To this end information previously stored in the evaluation system can also be used, e.g. empirically determined results.

Depending on the psychological state of the person which is detected by the measured values in the immediate vicinity of the eyes the evaluation system controls a stimulation system which sends stimulation signals of a predeterminable relaxing or tensing effect to the person. The person perceives the stimulation signals which in turn has effects on the psychological state of the person. Through this biofeedback of the biofeedback process according to the invention the stimulation signals are adapted to the relevant state of the psyche. The evaluation system thereby produces stimulation signals which are always different wherein the effect such as for example the relaxation or stimulation of the person is measured by the sensors and evaluated by the evaluation system.

With the biofeedback process according to the invention, stimulation signals are preferably transferred where a predefinable effect was shown or where such an effect can be predicted. If the biofeedback process is to be used for relaxing a person then preferably such stimulation signals are transferred where it has been shown that they have a relaxing effect on the person.

Depending on the intended use of the biofeedback process stimulation signals can however be transferred which set the person for example into a particularly creative mood.

In a preferred design of the biofeedback process according to the invention correlation means are used for determining a functional connection between the psychological states of the person and the stimulation signals. With such a functional connection it is possible to predict with great probability which effect a stimulation signal will have on the person.

In an advantageous design of the biofeedback process the evaluation system uses means which can be learnt and which generate independently new stimulation signals or complex patterns of stimulation signals. After a training phase the biofeedback process can be adapted particularly well to the person and creates an optimized effect on the psychological state. Such learnable (or adaptive) means use in particular artificial neural networks which are particularly suitable for analyzing connections which cannot be detected deterministically. Also artificial neural networks are particularly suitable for evaluating complex patterns such as for example measuring rows of physiological parameters.

Advantageously with the biofeedback process according to the invention the musculation potentials of the eye muscles and/or the eye movements are measured to determine the general psychological tension state. These measurements are carried out without great expense.

In another advantageous design of the biofeedback process muscle impulses or potentials in the nose root area are to be measured since it has been shown that specific evidence on the stressed state of the person can be obtained from this. These measurements can also be carried out without great expense.

Acoustic stimulation signals can also be used advantageously to affect the psyche. Frequency and/or amplitude-modulated tones are also preferably used. However complex sound patterns can also be used, more particularly filtered rustling noises or vibrations with breaks in between. Natural noises can also be used with advantage, such as for example the sound of the ocean, or spoken words. Acoustic stimulation signals of this kind are simple to produce and modify so that a rapid flexible adaptation of the stimulation signals to the psychological state of the person is possible. It is within the idea according to the invention to combine the various stimulation signals together so that for example the sound of the ocean can be combined with the spoken word.

In an advantageous design of the biofeedback process according to the invention the frequency or frequency spectrum and the volume of the acoustic stimulation signals are directly controlled by the eye movements of a person.

In a further design of the biofeedback process the person can likewise advantageously act directly on the evaluation system through a control element. Thus the person can consciously indicate whether he finds the stimulation signals acceptable or not acceptable. In connection with the measurements of the physiological parameters a comprehensive picture of the effect of the stimulation signals is thus obtained.

Advantageously the stimulation signals are terminated through a time switch or brought into another phase of a therapy program. It is likewise advantageous if certain boundary values are predetermined in the evaluation system to prevent particularly unacceptable or even damaging stimulation signals from being transferred to the person.

In a further advantageous design of the biofeedback process according to the invention the stimulation system stimulates the person through temperature, smell or color stimulus.

In a particularly expedient design of the biofeedback process the evaluation system exchanges data with an external data processing unit through an interface.

A device according to the invention for carrying out the biofeedback process has sensors for measuring movements and/or physiological parameters of the eyes, the eye muscles and/or muscles at the nose root. These measuring spots are readily accessible; more particularly the person does not have to undress in order to attach the sensors. An evaluation system of the device according to the invention serves to process measured values and evaluate the psychological state of the person and a stimulation system transfers stimulation signals to the person.

The evaluation system preferably has correlation means for determining a functional connection between the evaluations of the psychological states and the stimulation signals. With the correlation means it is possible to obtain a prediction on the effect of the stimulation signals on a person.

In a particularly advantageous embodiment the evaluation system has learnable (or adaptive) means, more particularly artificial neutral networks. Through learnable means the evaluation system can develop independent stimulation signals or patterns of stimulation signals which are each adapted in optimum manner to the psychological state of the person.

The evaluation system advantageously has an interface through which data can be exchanged with external data processing equipment. In this way remote-controlled monitoring of the evaluation system and stimulation system is possible.

These sensors can advantageously be mounted on a spectacles-like frame which has an interface for data lines and is connected through same to the evaluation system.

In a preferred embodiment the stimulation system is designed as a sound generator, more particularly as a synthesizer with which a plurality of sounds and tones can be readily produced. Also with sound generators very compact structural forms are possible.

Advantageously the stimulation system has a random access memory system. It is thereby possible to use for example a CD ROM or hard disc. In particular, natural sounds or spoken words can be stored in the random access memory system. The evaluation system can rapidly and accurately access individual stored information in dependence on the evaluation of the psychological state of the person and transfer this information as stimulation signals to the person.

In a further advantageous embodiment the device according to the invention has elements for producing the right temperature or generators for visual stimulation signals of the person.

A likewise advantageous embodiment of the device according to the invention has indicators for the measured physiological parameters.

BRIEF DESCRIPTION OF THE DRAWINGS

The invention will now be explained below with reference to the figures in the drawings showing several embodiments. In the drawings:

FIG. 1 is a diagrammatic view of a biofeedback process according to the invention and a device for carrying out the process;

DETAILED DESCRIPTION

Figure 2A:
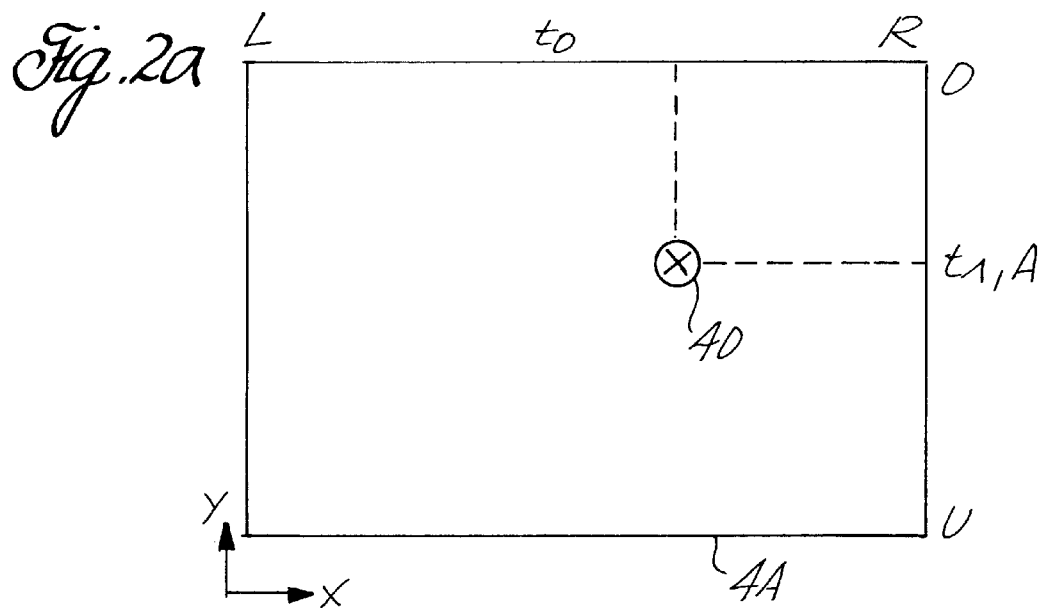
FIG. 2a is a diagrammatic illustration showing the measuring of the eye movements of a person.

FIG. 1 shows a diagrammatic illustration of a biofeedback process according to the invention and a device for carrying out the biofeedback process.

The basis of the present invention is that measurable physiological muscle parameters or measurable effects of muscle movements are suitable for detecting the psychological state of a person, and that the psychological state can be affected by stimulation signals 4. According to the invention the muscles in the immediate eye vicinity can be used in order to detect the psychological tension state.

More particularly it has been shown that eye movements 21 are a mirror image of the general psychological state of a person. Especially the stressed state of a person can be detected accurately through measurements of nerve impulses in the area of the nose root 22.

In the example illustrated here a person is to be sent into a relaxed state through the biofeedback process according to the invention. It has been shown that a filtered rustling noise evidently has a relaxing effect so that it is particularly suitable as an acoustic stimulation signal 4 for relaxing the person. The properties of the filtered rustling noise can be changed by changing the bandwidth and the mean frequency so that the end effect is a noise like the sound of the ocean.

If measurements of the physiological parameters which characterize the psychological tension state of the person and the generation of acoustic stimulation signals 4 are coupled together then a feed back 9 takes place in the human body which is also termed biofeedback. When using suitable stimulation signals 4 a biofeedback process of this kind leads to relaxation and the breakdown of stress.

To carry out the biofeedback process according to the invention sensors 1a are mounted on a spectacles frame 8 to measure the action potential of the eye muscles which are responsible for the eye movements 21. By attaching sensors 1a in the eye area the activities of the various eye muscles are detected from which the eye movements 21 can be derived. As sensors 1a can be for example silver or gold electrodes which are in contact with the skin.

In alternative embodiment of the biofeedback process the eye movements 21 are detected directly through measuring the line of sight (FIG. 2).

Furthermore sensors 1b are mounted on the spectacle frame 8 to measure the nerve impulses in the nose root area 22. In an alternative embodiment the muscle tensions in the area of the nose root 2 are detected through expansion measuring strips.

In addition to these measurements the person can also undertake an evaluation of the stimulation signals received using a control element 12, such as e.g. a slide ruler. Depending on the sensations the person evaluates his psychological state by operating the slide ruler through a scale (e.g. from 'feeling very positive' to 'feeling very negative'). Through such a control element 12 it is also possible to determine for example whether the person finds a stimulation as conveying particular creativity.

The measured values of the musculation potentials and nerve impulses recorded by the sensors 1a, 1b are transferred to an amplifier 11 through an interface 10 mounted in the spectacle frame 8. By integrating the data lines for the measured signals and interface 10 in the spectacle frame 8 a device is produced which is compact and comfortable to wear.

The measured values are transferred from the amplifier 11 to an evaluation system 2 which stores and processes the measured values. The signals coming in from the control element 12 are sent to the evaluation system 2. As evaluation system 2 can be used as a rule a computer in which programs are stored for analyzing the measured values and also information for interpreting these measured values. In general the analysis of the measured values can be provided as both a hardware and software solution.

The measured values for the eye movements 21 are thereby used to assess the general psychological state of the person. From the measurements of the nerve impulses in the nose root area 22 it is possible to conclude the stressed state (i.e. relaxation/tensing) of the person. Both measurements are correlated by programs stored in the evaluation system 2 and used to evaluate the psychological state of the person. The information which was stored previously in the evaluation system 2 also serves for this purpose. Thus for example already known connections between muscle action potentials and the relaxation state of a person are stored in the evaluation system.

The evaluation system 2 controls in dependence on the evaluation of the psychological tension state a stimulation system 3 which transfers acoustic stimulation signals 4 to the hearing 5 of the person. The stimulation system 3 has a synthesizer so that both simple sine tones and also complex sound patterns can be used to stimulate the person.

Part of the stimulation system 3 is a CD ROM on which a number of spoken words with calming effect are stored. The evaluation system 2 can access these words word-perfect and can transfer them in a selective sequence as stimulation signals 4 to the person. On another CD ROM natural sounds are stored which can be selected in similar way by the evaluation system 2. The evaluation system can control the stimulation system 3 so that different stimulation signals are superimposed. Thus for example a filtered rustling noise can be used in connection with words. In alternative embodiments other random memory systems can be used such as for example hard disc drives for storing information.

Boundary values for stimulation signals 4 are stored in the evaluation system 2 to prevent unacceptable stimulation signals 4 from being transferred to the person.

The person hears different acoustic stimulation signals 4 and reacts each time in a different way. Many stimulation signals 4 are felt to be relaxing whilst others are felt to be stimulating. The changes in the psychological tension state produced through the acoustic stimulation signals 4 are detected by the sensor 1a, 1b and evaluated by the evaluation system 2. Thus a feed back 9 (bio feedback) takes place in the human body.

Since it is the aim of the biofeedback process illustrated here by way of example to relax the person acoustic stimulation signals 4 transferred to the person are preferably those where a relaxing effect has previously been measured or a relaxing effect can be predicted.

The evaluation system 2 stores all incoming measured values, the evaluations of the psychological state and the acoustic stimulation signals 4 which are transferred to the person. The evaluation system 2 has a correlation program with which a functional connection is produced between the evaluations of the psychological tension state and the acoustic stimulation signals 4. Through such correlation it is possible to predict acoustic stimulation signals 4 at which a relaxing action will in all probability occur. The evaluation system 2 thereby not only checks the short-term effects on the psyche of the person but also examines whether there are complex longer signal patterns which produce a particularly lasting relaxation of the person. Through continued improvement in the correlation between the psychological tension state and the acoustic stimulation signals 4 it is possible to reach an optimized relaxation of the person.

For an adaptive formation of relaxing signal patterns the evaluation system 2 also has as learnable programs artificial neural networks which are particularly suitable for detecting complex and deterministically poorly formulating connections. Through the training of such artificial neural networks the evaluation system 2 according to the invention develops independently stimulation patterns which have a particularly good relaxing effect on a person. A feedback of the higher order is produced.

The data stored in the evaluation system 2 can also be used for research purposes wherein for example stimulation patterns are identified which generally lead to relaxation. Long term investigations can also be carried out wherein inter alia changes in the relaxation behavior of a person under the effect of medication are examined.

For the direct evaluation of the measured results the evaluation system (2) has indicators on the measured psychological parameters. A therapist can thus read off directly which values are measured and how they have changed.

The evaluation system 2 has an interface 13 with which information is transferred to an external data processing unit 14. Thus it is possible that a therapist monitors the work of the biofeedback process according to the invention without actually being in the vicinity of the person. Should it be necessary then the therapist can take controlling action. It is also possible to send the information stored in the evaluation system 2 via this interface 13 to a central computer e.g. in a hospital. Thus for example a medicine dispenser can be linked to the device according to the invention. The effect of the medicaments on the psychological state of the person is then detected through the measurements of the physiological muscle parameters by the evaluation system 2 whereby the stimulation signals 4 are changed according to the provisions of the process.

However the evaluation system 2 can also directly control the medicine dispenser. If for example a clear relaxation of the person is registered then the supply of sedating medicament is cut back.

In alternative embodiments of the invention other perceptive senses 5 of the person can also be stimulated apart from the hearing. Thus in dependence on the measured muscle parameters and evaluation of the psychological state of the person, temperature stimulus can be passed to the person through heating elements. Optical signals with different colors or different perfumes can also be used as stimulation signals 4. It is within the scope of the present invention to use several stimulation signals in combination.

In FIGS. 2a to 2d a further embodiment is shown diagrammatically for measuring the eye movements 21 and influencing acoustic stimulation signals 4. The eye movements 21 of the person are hereby detected through a known system for determining the line of sight. The line of sight can thereby be focused into a spot-like sight focus 40 which can be represented in a Cartesian co-ordinate system 41.

The movements of the sight focus 40 in the co-ordinate system 41 are used by the evaluation system 2 for controlling the stimulation system 3. Frequency and/or amplitude tones or sounds are thereby generated as stimulation signals 4.

Figure 2B:
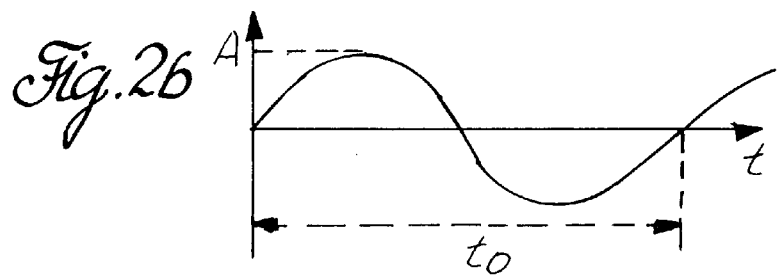
FIG. 2b shows a pure sine tone as an acoustic stimulation signal.

FIGS. 2a and 2b show how different abscissa and ordinate values of the sight focus 40 are used for controlling the stimulation system 3. If the eyes 7 move from left L to right R (i.e. the abscissa value to of the sight focus 40 becomes bigger) then the wave length of the tone 4 given out becomes longer and the person hears an increasingly lower tone 4. If the eyes 7 move from top O to bottom U (i.e. the ordinate value A of the sight focus 40 becomes smaller) then the amplitude of the tone 4 becomes smaller and the person hears an increasingly lighter tone 4. Since the sight focus 40 is moved in the overall co-ordinate system 41 the frequencies and amplitudes of the tones 4 are changed at the same time.

Figure 2C:
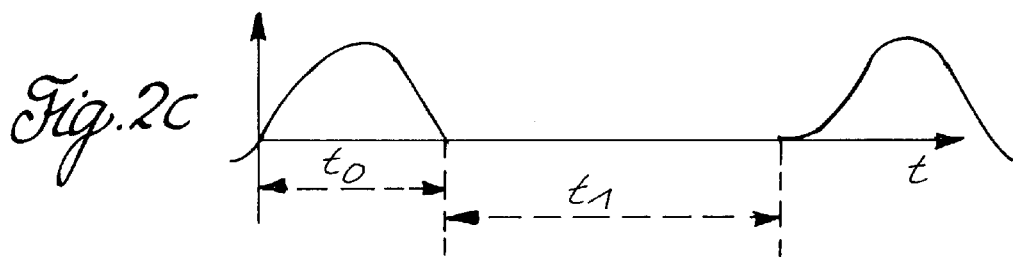
FIG. 2c illustrates an acoustic stimulation signal with interruption.

FIG. 2c shows another control of the acoustic stimulation signals 4. The abscissa value $t_0$ of the sight focus 40 hereby determines the wave length $t_0$ of a vibration which is stopped after a certain number of vibrations. The ordinate value $t_1$ of the sight focus 40 determines the interval length $t_1$ after which the vibration is inserted again.

Figure 2D:
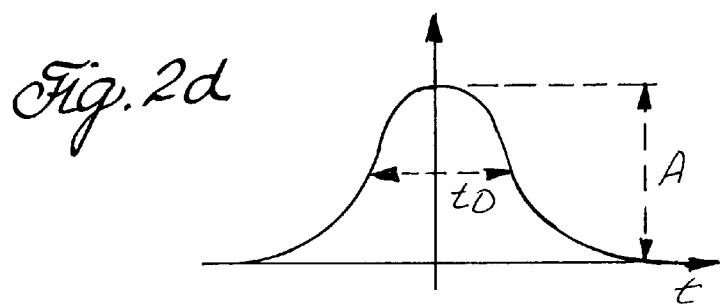
FIG. 2d illustrates a non-sinusoidal acoustic stimulation signal.

FIG. 2d shows a section of an acoustic non-sinusoidal periodic stimulation signal 4 whose amplitude is determined by the ordinate value 6A of the sight focus 40 whilst the width of the signal follows from the abscissa value $t_0$.

The invention is not restricted in its design to the preferred embodiments described above. Rather a number of variations is possible which utilize the biofeedback process according to the invention and the device for carrying out the biofeedback process for affecting the psyche of a person even in fundamentally different designs.

What is claimed is:

1. A biofeedback process for producing acoustic and/or optical signals for relaxation purposes comprising:

electrically measuring eye movements of a person to obtain measured values by detecting action potentials in an eye and/or nose root area by sensors;

transferring the measured values to an evaluation system having information allotted to the measured values;

producing control signals for a stimulation system on the basis of the detected measured values and the information allotted to the measured values and stored in the evaluation system;

substantially continuously producing acoustic and/or optical signals from the stimulation system, in dependence on the control signals; and delivering the produced acoustic and/or optical signals so that they are detected by at least one perceptive sense of the person.

2. The biofeedback process according to claim 1 wherein the acoustic and/or optical signals are frequency and/or amplitude modulated tones or color signals.

3. The biofeedback process according to claim 1 wherein the acoustic and/or optical signals are natural sounds, spoken words, rustling noises with variable bandwidth and mean frequency or vibrations with interposed interruptions.

4. The biofeedback process according to claim 1 wherein producing the acoustic and optical signals further comprises retrieving the acoustic and/or optical signals from a memory system.

5. The process according to one of the preceding claims further comprising correlating the produced measured values relating to the eye movements of the person and the produced acoustic and/or optical signals together through correlation programs of the evaluation system so that a functional connection is produced between the eye movements and the acoustic and/or optical signals perceived by the person.

6. The process according to claim 5 further comprising developing, through the evaluation system and the stimulation system, independent acoustic and/or optical signals which lead to an influence on the eye movements of the person.

7. The process according to claim 6 further comprising using artificial neuronal networks for developing the independent acoustic and/or optical signals.

8. The process according to claim 2 further comprising influencing the frequency or the frequency spectrum, and the volume of the acoustic signals directly by the eye moment.

9. The process according to claim 1 wherein the sensors that measure the action potentials of the eyes detect eye movements.

10. The process according to claim 9 wherein the sensors that measure eye movements also measure nerve impulses of muscles in the area of the nose root, and the nerve impulses serve as a starting value for the control signals produced by the evaluation system.

11. The process according to claim 1 further comprises providing signals of a control element that is operable by the person as a starting value for the control signals produced by the evaluation system.

12. A device for implementing a biofeedback process producing acoustic and/or optical signals for relaxation purposes comprising:

sensors that detect measured values by electrically measuring eye movements of a person, wherein the sensors detect action potentials in the eye and/or nose root area;

an evaluation system to which the measured values detected by the sensors are transferred, and the evaluation system has a control signal producer that produces control signals on the basis of the measured values and data which is allotted to the measured values and stored in the evaluation system;

a stimulation system that substantially continuously generates acoustic and/or optical signals in dependence on the control signals; and a transporter that sends the generated acoustic and/or optical signals to the person.

13. The device according to claim 12 wherein the evaluation system has correlation programs for determining functional connections between the measured values and the acoustic and/or optical signals.

14. The device according to claim 12 or 13 wherein the evaluation system, through the stimulation system, produces acoustic and/or optical signals suitable for influencing the eye movements and thus psyche of the person.

15. The device according to claim 14 wherein the evaluation system has artificial neuronal networks that produce the acoustic and/or optical signals suitable for influencing the eye movements and psyche of the person.

16. The device according to claim 12 wherein the sensors are mounted on a spectacles frame and the spectacle frame has an interface for data lines.

17. The device according to claim 12 wherein the stimulation system has a sound generator or a synthesizer.

18. The device according to claim 12 wherein the stimulation system has at least one memory system wherein the evaluation system can access individual information stored on the memory system.

19. The device according to claim 18 wherein the stimulation system has a CD ROM player as the memory system.

20. The device according to claim 12 wherein the stimulation system has elements for creating an optimal temperature and/or generators for optical signals.

21. The device according to claim 12 wherein the evaluation system has indicators for the measured values.

* * * * *